United States Patent [19]

Renovanz et al.

[11] 3,990,295

[45] Nov. 9, 1976

[54] APPARATUS AND METHOD FOR THE PERFORMANCE OF CAPILLARY VISCOSIMETRIC MEASUREMENTS ON NON-HOMOGENEOUS LIQUIDS

[75] Inventors: Hans-Dietrich Renovanz, Biberach; Karl Heissler, Nurnberg; Eberhard Weller, Biberach, all of Germany

[73] Assignee: Boehringer Ingelheim GmbH, Ingelheim am Rhein, Germany

[22] Filed: Sept. 15, 1975

[21] Appl. No.: 613,069

[30] Foreign Application Priority Data
Sept. 16, 1974 Germany.......................... 2444148

[52] U.S. Cl. .................................................. 73/55
[51] Int. Cl.² ........................................ G01N 11/08
[58] Field of Search ........................................ 73/55

[56] References Cited
UNITED STATES PATENTS
1,962,861  6/1934  Ericson .................................. 73/55
3,911,728  10/1975  Fixot .................................... 73/55

Primary Examiner—Richard C. Queisser
Assistant Examiner—Joseph W. Roskos
Attorney, Agent, or Firm—Hammond & Littell

[57] ABSTRACT

A device for making accurate capillary-viscosimetric measurements on non-homogeneous liquids of all types, and especially on biological liquids, such as human sputum samples; the device consists essentially of a cylinder comprising a plunger, a capillary tube, a pressure recorder, means for exerting a constant pressure upon said plunger, and a T-shaped adapter which provides communicating channels between the cylinder, the capillary tube and the pressure recorder.

6 Claims, 2 Drawing Figures

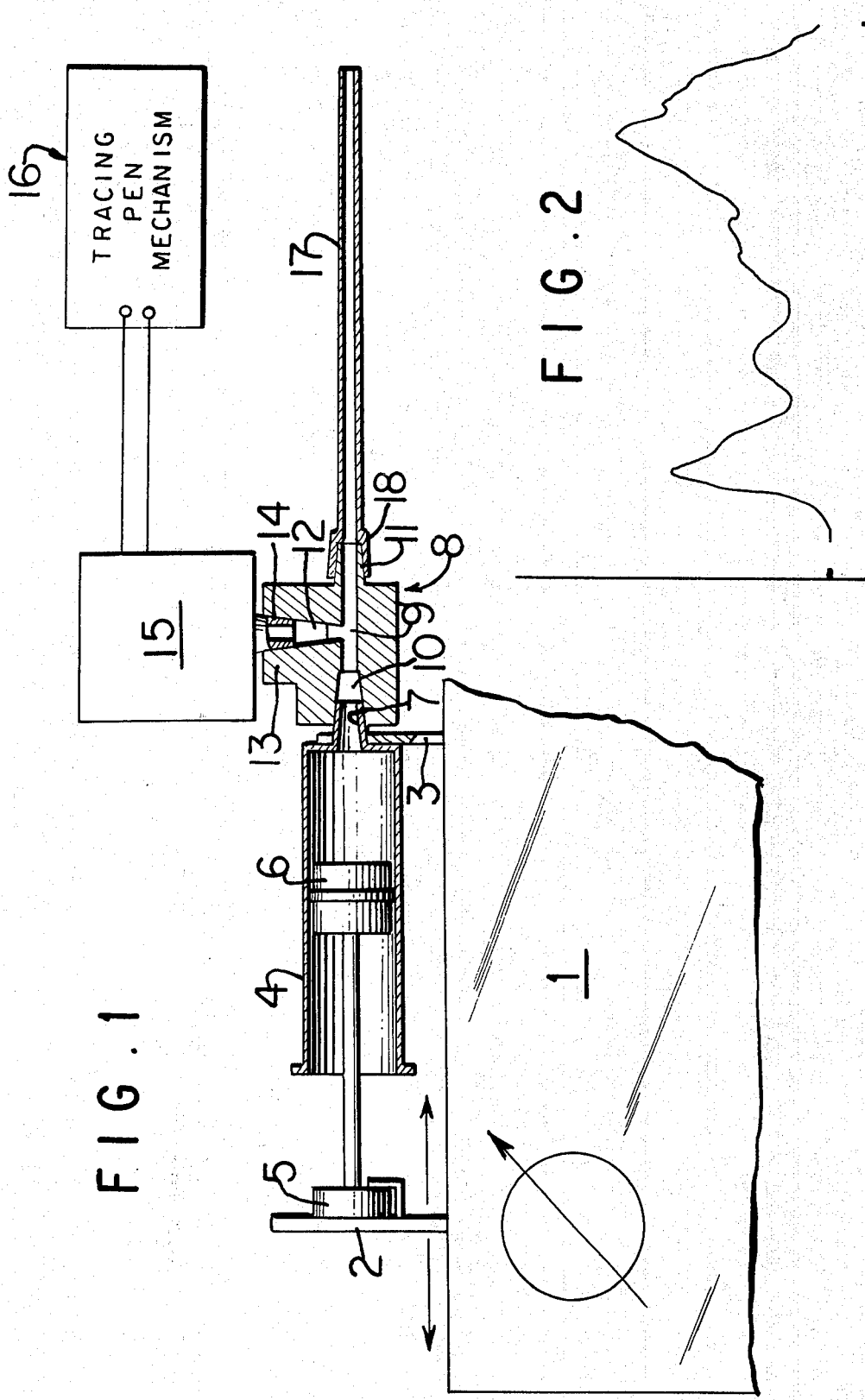

APPARATUS AND METHOD FOR THE PERFORMANCE OF CAPILLARY VISCOSIMETRIC MEASUREMENTS ON NON-HOMOGENEOUS LIQUIDS

This invention relates to a novel apparatus and method for making accurate capillary-viscosimetric measurements on non-homogeneous liquids, particularly on human sputum samples.

BACKGROUND OF THE INVENTION

Mucous membrane secretions are non-homogeneous solutions of long-chain macromolecular substances. The non-homogeneous character of the mucous membrane secretions, which may often be mixed with some very viscous lumps, makes it impossible to make viscosimetric measurements thereon with the usual capillary viscometers. The free flow through the capillaries based on the gravity and the height differential within the vertical capillaries, is interrupted by clogging as soon as viscous lumps of mucus enter the tubes; measurement of the time of throughflow, therefore, becomes impossible.

M. W. Arveson has constructed a capillary viscometer wherein highly viscous fats are forced through a capillary by means of a piston, where the required pressure is measured. However, this apparatus is not suitable for measuring small non-homogeneous quantities of sputum such as those obtained in clinical examinations. The apparatus is, moreover, very expensive to build and extremely unwieldy. Therefore, S. R. Hirsch and R. O. Kory [J. Allergy 39, 265 (1967)] later developed a sputum viscometer wherein the sputum is forced through a perforated hypodermic syringe piston, while the pressure developed thereby is measured. This apparatus gives insufficiently accurate values, however, since no true capillary effect is achieved, and thus laminar flow is not assured. In addition, it is impossible or possible only to a limited extent, to determine different measurement parameters which are important to the evaluation of human sputum or a therapeutic agent which affects it. For a meaningful evaluation of a sputum sample, it is necessary that, first, the overall viscosity of this sputum sample can be measured and, secondly, that the maximum and minimum viscosities of this sputum sample can be determined. It has become evident that conventional viscometers, such as capillary viscometers, falling sphere viscometers and rotation viscometers, are inadequate for determination of these values on non-homogeneous human sputum samples which are solutions of restricted volume and do not follow Newton's law.

OBJECT OF THE INVENTION

It is an object of the present invention to provide a device with the aid of which it is possible to make accurate viscosity measurements on non-homogeneous liquids of limited volume, such as human sputum samples or the like, wherein large differentials of viscosity exist.

Other objects and advantages of the present invention will become apparent as the description thereof proceeds.

THE INVENTION

The above object is achieved by means of the device of the present invention which consists essentially of a T-shaped connecting element comprising a longitudinal bore passing through the cross-bar of the T and a lateral bore at substantially right angles to and communicating with the longitudinal bore; a cylinder comprising a slidable piston, said cylinder being connected to one end of the longitudinal bore; a capillary tube connected to the other end of the longitudinal bore; a pressure-sensitive recording device connected to the outer end of the lateral bore; and means for applying a constant force upon the slidable piston. The diameter of the longitudinal bore must be greater than the internal diameter of the capillary tube.

A commercial hypodermic syringe is preferably used as the cylinder comprising a piston, which, after drawing up the liquid sample, is inserted with its male conical end into a corresponding female fitting in the longitudinal bore of the T-shaped connecting element. A stainless steel capillary tube is used as the capillary; it comprises an internal conical fitting which is placed on the other end of the longitudinal bore which is provided with a corresponding external conical extension. The pressure recorder, for example, an apparatus with a wire strain gauge or a piezoelectric or inductive pressure transducer, is inserted, preferably at right angles to the hypodermic syringe, into a female conical or threaded fitting in the outer end of the lateral bore. The pressure receiver is connected to a tracing pen.

The plunger of the syringe is moved forward evenly by means of a pusher device which is preferably continuously regulatable, so that a constant rate of flow of the liquid to be tested is obtained. An infusion pump, such as is conventionally available in hospitals, is suitable as the pusher device, for example.

The apparatus works as follows: After the liquid to be tested for viscosity has been drawn up into the hypodermic syringe, the latter is inserted in the T-shaped connecting element. When the pusher device is turned on, the air present in the cannula (syringe) is first compressed. The pressure recorder measures the pressure present immediately in front of the capillary. The pusher device is then briefly turned off and the "zero" pressure now present after the pressure exchange is set at the desired base line on the recorder. The pump is then turned on again, and the actual measurement begins.

When subsequently measuring another liquid, it is not necessary to rinse the cannula, since the very small dead space (0.05 ml, for example) permits a rapid exchange of the liquid to be tested.

The length (abscissa) of the curve recorded by the tracing pen is a measure of the quantity of liquid measured when the rate of flow is known and constant.

The amplitude of the deviations (ordinate) is a measure of the viscosity. The "average viscosity" can be obtained by integration and subsequent division by the length of the curve. Maximum and minimum values of the viscosity can be read off directly.

The parameters chosen in each case (cannula, rate of flow) can be calibrated, using a liquid of known viscosity.

The accuracy of the measurement is determined by the precision of the pusher device which must guarantee a constant strength of flow (rate of flow). It is also important that, because of the thizotropic properties of human sputum, measurements on human sputum are not made at too slow a rate of flow, unless these properties are to be especially included.

The great advantage of the apparatus according to the invention resides in the fact that large variations in viscosity within one sample can be accurately measured, the quantity of the sample is not limited, and that the apparatus can be used as a true capillary viscometer for series examinations, without needing to wait each time. A small dead space in the T-shaped connecting element permits the performance of viscosity measurement on liquid quantities of about 0.2 ml. The most advantageous diameter range of the capillary is between 0.3 and 0.8 mm; it is advantageous to work with a liquid flow rate of about 0.1 to 0.6 ml/minute. Another great advantage is the fact that standardized single-use, disposable syringes can be used, which, according to our experience, have only insignificant tolerances, so that it is not necessary to clean the cylinder and piston element of the apparatus.

Brief reference should also be made to the physical basis of this method of measuring viscosity; from the equation $$\eta = \frac{\Delta p \times \pi \times r^4}{8 \times 1 \times l}$$

wherein $\eta$ represents the viscosity in dyne.sec.cm$^{-2}$ $\Delta p$ represents the pressure in microbars, $r$ is the radius of the capillary in cm, $l$ is the length of the capillary in cm, I is the liquid flow rate, expressed by the ratio of volume (ml) divided by the time of throughflow (sec), it can be seen that the viscosity can be determined by measuring the variable pressure $p$, if all the other values are kept constant. This pressure $\Delta p$ is necessary to press the liquid through the capillary at a constant rate of flow I.

The essential features of the apparatus according to the invention are shown in the attached drawing, of which FIG. 1 is a schematic representation of the apparatus according to the present invention, and FIG. 2 is a typical viscosity curve of a sample of human sputum recorded by the tracing pen connected to the pressure recorder of the apparatus of this invention.

Referring now to FIG. 1 of the drawing the apparatus of the present invention consists of a continuously regulatable pushing device 1, such as an infusion pump with constant feed, comprising a movable carrier 2 for the syringe plunger and a fixed support 3 for the syringe; a hypodermic syringe 4 comprising a plunger 5, a piston 6 and a conical end 7; a T-shaped adapter 8 comprising a longitudinal bore 9 which has an internal female conical fitting 10 to receive the male conical end 7 of the syringe 4, and an external male conical extension 11; a lateral bore 12 which has an internal female conical or threaded fitting 13 to receive a male conical or extended fitting 14 of a pressure-sensitive transducer 15 which is connected to a tracing pen mechanism 16; and a capillary tube 17 whose female conical extension 18 fits over the male conical extension 11 of the T-shaped adapter 8.

It should be understood that the use of the abovedescribed apparatus according to the present invention is not restricted to making capillary-viscosimetric measurements on human sputum samples. It can also be used for making such measurements on other liquids, especially non-newtonian liquids, for example on biological liquids, on non-homogeneous oils, on liquid non-homogeneous plastic materials or solutions containing such materials, or on suspensions of pigments of varying sizes and chemical nature.

While the present invention has been illustrated with the aid of a certain specific embodiment thereof, it will be readily apparent to others skilled in the art that the invention is not limited to this particular embodiment, and that various changes and modifications may be made without departing from the spirit of the invention or the scope of the appended claims

We claim:

1. An apparatus for making capillary-viscosimetric measurements on non-homogeneous or homogeneous non-newtonian liquids, said apparatus consisting essentially of a T-shaped element comprising a first bore extending longitudinally through the cross-bar of the T and a second bore extending longitudinally through the stem of the T and communicating with said first bore; a cylinder having a longitudinally slidable piston therein, said cylinder being connected to one end of said first bore; a capillary tube connected to the other end of said first bore; said first bore, said cylinder and said capillary tube being in axial alignment with respect to each other, and the diameter of said first bore being larger than the internal diameter of said capillary tube; a pressure-sensitive recording device connected to said second bore; and means for advancing said piston at a constant rate through said cylinder toward said first bore.

2. An apparatus of claim 1, wherein said cylinder comprising a slidable piston is a hypodermic syringe.

3. An apparatus of claim 1, wherein said capillary tube is a stainless steel capillary which is connected to said first bore by means of a threaded fitting seated over a correspondingly threaded extension of said first bore.

4. An apparatus of claim 1, wherein said lateral bore is at an angle of 90° to said first bore.

5. An apparatus of claim 1, wherein said means for advancing said piston is continuously regulatable.

6. The method of making capillary-viscosimetric measurements on a non-homogeneous or homogeneous non-newtonian liquid, which comprises forcing said liquid at a uniform rate through the first bore of an apparatus of claim 1 until the air in said bore has been displaced, measuring the initial pressure created thereby, and subsequently forcing said liquid at a constant flow rate through said capillary while measuring the final pressure created thereby.

* * * * *

PO-1050
(5/69)

UNITED STATES PATENT OFFICE
CERTIFICATE OF CORRECTION

Patent No. 3,990,295      Dated November 9, 1976

Inventor(s) HANS-DIETRICH RENOVANZ, KARL HEISSLER and EBERHARD WELLER

It is certified that error appears in the above-identified patent and that said Letters Patent are hereby corrected as shown below:

Col. 4 Line 46     "lateral" should read -- second --

Signed and Sealed this

Eleventh Day of January 1977

[SEAL]

Attest:

RUTH C. MASON
*Attesting Officer*

C. MARSHALL DANN
*Commissioner of Patents and Trademarks*